United States Patent [19]

Ishikawa et al.

[11] Patent Number: 5,895,855

[45] Date of Patent: Apr. 20, 1999

[54] ULTRASONIC PROBE TRANSMITTING/ RECEIVING AN ULTRASONIC WAVE OF A PLURALITY OF FREQUENCIES AND ULTRASONIC WAVE INSPECTION APPARATUS USING THE SAME

[75] Inventors: Yuko Ishikawa, Abiko; Yukio Ito, Machida; Hiroshi Kanda, Tokorozawa, all of Japan

[73] Assignee: Hitachi Medical Co., Tokyo, Japan

[21] Appl. No.: 08/815,856

[22] Filed: Mar. 12, 1997

[30] Foreign Application Priority Data

Apr. 12, 1996 [JP] Japan .................................. 8-114353

[51] Int. Cl.$^6$ .................................................. G01N 29/24
[52] U.S. Cl. ............................ 73/632; 310/320; 310/322
[58] Field of Search ............................ 73/644, 628, 612, 73/642, 597, 629, 632, 649; 310/320, 324, 321–323, 325, 328–332, 334, 336–337, 348, 367–369

[56] References Cited

U.S. PATENT DOCUMENTS

| | | |
|---|---|---|
| 3,569,750 | 3/1971 | Beaver ........................ 310/320 |
| 3,924,454 | 12/1975 | McElroy et al. ................ 73/628 |
| 3,952,216 | 4/1976 | Madison ..................... 310/325 |
| 4,490,640 | 12/1984 | Honda ....................... 310/325 |
| 4,633,119 | 12/1986 | Thompson ................... 310/325 |
| 4,870,972 | 10/1989 | Maerfeld et al. ............ 600/459 |
| 5,460,595 | 10/1995 | Hall et al. ................. 310/320 |
| 5,706,252 | 1/1998 | LeVerrier et al. ........... 367/152 |

*Primary Examiner*—Hezron Williams
*Assistant Examiner*—Rose M. Miller
*Attorney, Agent, or Firm*—Antonelli, Terry, Stout & Kraus, LLP

[57] ABSTRACT

In an ultrasonic inspection apparatus, a piezoelectric element having a first resonant frequency is stuck to a complex resonance member having a second resonant frequency. The second resonant frequency is determined with a conversion in terms of half wavelength. A resultant ultrasonic probe transmits/receives ultrasonic waves of the first resonant frequency and a plurality of other frequencies. In constructing an ultrasonic tomographic image of the object to be inspected from a received signal obtained by using the ultrasonic probe, the imaging frequency is changed according to the depth in the object to be inspected.

27 Claims, 4 Drawing Sheets

ULTRASONIC PROBE TRANSMITTING/RECEIVING AN ULTRASONIC WAVE OF A PLURALITY OF FREQUENCIES AND ULTRASONIC WAVE INSPECTION APPARATUS USING THE SAME

BACKGROUND OF THE INVENTION

The present invention relates to an ultrasonic probe of an ultrasonic apparatus for acquiring information from inside of an object to be inspected and discriminating a structure or a tissue included in the object to be inspected on the basis of the acquired information, and relates to an ultrasonic inspection apparatus using such an ultrasonic probe.

Conventionally, it has been conducted in the medical and nondestructive inspection fields to transmit an ultrasonic wave into an object to be inspected, measuring an echo signal reflected within the object to be inspected or an ultrasonic wave transmitted through the object to be inspected, and discriminate a structure or a tissue included in the object to be inspected. In such an ultrasonic apparatus, an ultrasonic probe is used to transmit an ultrasonic wave to the object to be inspected and receive a signal brought about by the object to be inspected.

An ultrasonic wave is generated by applying a voltage of approximately 400 V to electrodes of piezoelectric elements included in the probe. It is known that continuously applying a voltage to the electrodes with a certain specific frequency causes an ultrasonic wave having the resonant frequency to be generated whereas applying a voltage in a pulse form causes an ultrasonic wave having a certain band around a center frequency equivalent to a resonant frequency of the piezoelectric elements to be radiated from the probe.

If an ultrasonic wave transmitted or received by a conventional probe is subjected to frequency analysis, only one signal having the resonant frequency of the piezoelectric elements is obtained as a high gain signal.

In the object to be inspected, the ultrasonic wave is attenuated more strongly as the region to be inspected becomes becomes deeper. And the attenuation ratio becomes greater as the frequency of the ultrasonic wave is made higher. In an apparatus for imaging a signal obtained from the inside of the object to be inspected such as an apparatus used for medical image diagnosis, the spatial resolution of an obtained image becomes better as the frequency of the ultrasonic wave is made higher. In other words, a favorable image of a shallow region of the object to be inspected is obtained by using a probe having a high ultrasonic frequency.

If a probe having a high frequency is used to inspect a deep region, however, the ultrasonic wave is attenuated and a sufficient receiving sensitivity is not obtained. Eventually, a probe having a low ultrasonic frequency must be used for a deep region at the sacrifice of the spatial resolution. It was thus difficult to measure favorable signals from both a deep region and a shallow region of an object to be inspected simultaneously by using a single probe. In an adopted method, therefore, probes are used properly in a deep region and a shallow region of the object to be inspected in order to obtain images respectively. In this case, it is difficult to apply those probes to completely the same position of the object to be inspected and obtain images of the same region. In the case where the object to be inspected is a living body, organs and tissues within the living body move while probes are being exchanged. Even if the probes can be applied to the same region, therefore, it is difficult to obtain temporally the same image and the inspection efficiency is disadvantageously poor. Thus various attempts to widen the bandwidth of the probe have been made. Under the existing conditions, the width expansion as compared with the conventional probe is limited to a slight value.

SUMMARY OF THE INVENTION

A first object of the present invention is to provide such a novel probe that an ultrasonic wave having a wide range of frequency with the order of several MHz to several tens or several hundreds MHz can be inputted/outputted by using a single probe in order to solve the above described problems of the conventional technique.

In other words, the first object is to make it possible in the frequency range of several MHz to several hundreds MHz to transmit/receive an ultrasonic wave having a plurality of frequency spectra effective as signals by using a single probe.

A second object of the present invention is to provide an ultrasonic inspection apparatus for inspecting an object by using the probe having a wide range of frequency characteristics, which brings about accuracy of inspection and a high inspection efficiency. In particular, the second object is to provide an ultrasonic inspection apparatus capable of measuring the attenuation of ultrasonic waves caused by an object to be inspected and depicting the inside of the object to be inspected with the use of the probe according to the present invention.

In order to solve the above described subject (the first object), in accordance with the present invention, an ultrasonic probe of one channel includes a piezoelectric element having a predetermined first resonant frequency and a complex resonance member stuck to the piezoelectric element, the complex resonance member having a second resonant frequency different from the first resonant frequency, the complex resonance member inputting/outputting an ultrasonic wave of the resonant frequency of the piezoelectric element and a plurality of other frequencies. The complex resonance member generates and receives ultrasonic waves having a plurality of frequency spectra located at predetermined frequency intervals in both a higher frequency region and a lower frequency region around the resonant frequency of the piezoelectric element.

In order to solve the above described subject (the second object), in accordance with the present invention, an ultrasonic inspection apparatus includes an ultrasonic probe including a piezoelectric element having a predetermined first resonant frequency and a complex resonance member stuck to the piezoelectric element, the complex resonance member having a second resonant frequency different from the resonant frequency of the piezoelectric element, the complex resonance member inputting/outputting an ultrasonic wave of the resonant frequency of the piezoelectric element and other frequencies, a circuit for driving the ultrasonic probe and thereby transmitting/receiving the ultrasonic wave of the frequencies to/from an object to be inspected, and a circuit for measuring, from received signals, attenuation applied to the ultrasonic wave of the plurality of frequencies by the object to be inspected.

In order to solve the above described subject (the second object), in accordance with the present invention, an ultrasonic inspection apparatus includes an ultrasonic probe including a piezoelectric element having a predetermined first resonant frequency and a complex resonance member stuck to the piezoelectric element, the complex resonance member having a second resonant frequency different from the resonant frequency of the piezoelectric element, the complex resonance member inputting/outputting an ultrasonic wave of the resonant frequency of the piezoelectric element and other frequencies, a transmitting/receiving circuit for transmitting/receiving ultrasonic beams to/from an object to be inspected by using the ultrasonic probe and scanning the object to be inspected with the ultrasonic beams, a signal separation circuit for separating each of beam signals outputted by the transmitting/receiving circuit into a plurality of signals according to frequency, an image processing circuit for conducting image processing on for each of the signals with the same frequency outputted from said signal separation circuit and generating a plurality of sheets of image data, and an image display unit for displaying an output signal of the image processing circuit as an image. Furthermore, an image of a specific frequency can be selectively displayed on the image display unit from the image processing circuit.

In order to solve the above described subject (the second object), in accordance with the present invention, an ultrasonic inspection apparatus includes an ultrasonic probe including a piezoelectric element having a predetermined first resonant frequency and a complex resonance member stuck to the piezoelectric element, the complex resonance member having a second resonant frequency different from the resonant frequency of the piezoelectric element, the complex resonance member inputting/outputting an ultrasonic wave of the resonant frequency of the piezoelectric element and a plurality of other frequencies, a transmitting/receiving circuit for transmitting/receiving the ultrasonic beams to/from an object to be inspected by using the ultrasonic probe and scanning the object to be inspected with the ultrasonic beams, a signal separation circuit for separating each of beam signals outputted by the transmitting/receiving circuit into a plurality of signals according to frequency, a signal cutout circuit for determining a signal cutout area for each of signals separated by the signal separation circuit and cutting out a signal of that area, an image processing circuit for linking output signals from the signal cutout circuit in an order of frequency, executing the linking operation for each ultrasonic beam to generate one sheet of image data, and an image display unit for displaying an output signal of the image processing circuit as an image.

As heretofore described, the present invention makes it possible to transmit/receive an ultrasonic wave having an extra-high frequency of the order of several MHz to several tens or several hundreds MHz by using a single probe. By using this ultrasonic probe in an ultrasonic inspection apparatus, it is possible to measure ultrasonic attenuation in an object to be inspected with respect to a plurality of frequencies simultaneously. Furthermore, since a plurality of images ranging from a low frequency to a high frequency can be obtained from the inside of the object to be inspected in a single ultrasonic scan, images ranging from a shallow region to a deep region of the object to be inspected at the same time can be compared with each other. Furthermore, by using image information with a plurality of frequencies obtained by a single scan and thereby forming a resultant image linking signals having the highest resolution and sensitivity in respective depths of a sectional view of the object to be inspected, the accuracy and efficiency of inspection can be improved.

DESCRIPTION OF THE PREFERRED EMBODIMENTS

Figure 1A:
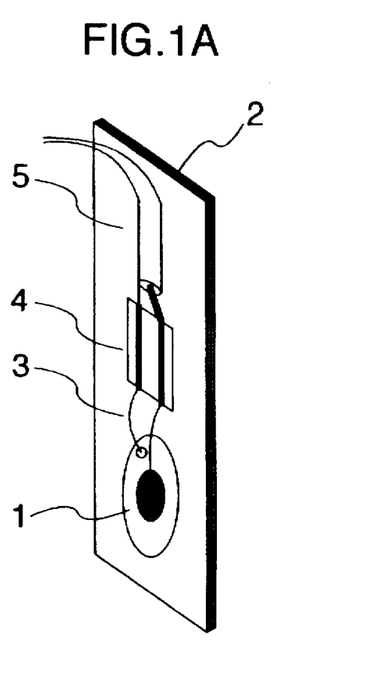
FIGS. 1A and 1B are diagrams showing an embodiment of an ultrasonic probe.
Figure 1B:
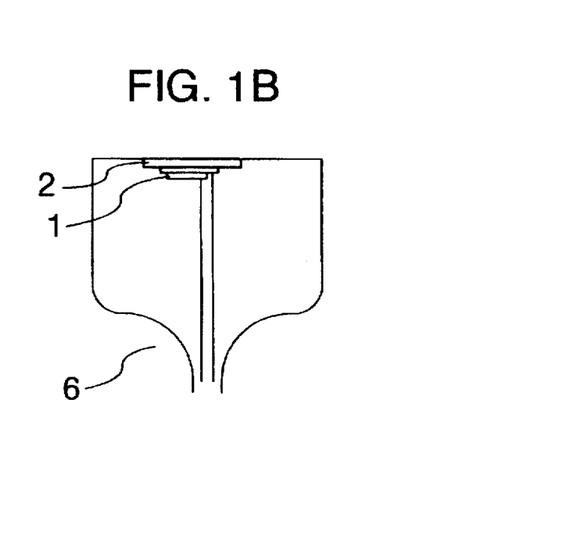

Hereafter, preferred embodiments of the present invention will be described by referring to the drawing. FIGS. 1A and 1B show the basic configuration of an ultrasonic probe according to the present invention. In FIGS. 1A and 1B, numeral 1 denotes a disk-shaped PZT piezoelectric element having an extra-high frequency as the resonant frequency. Numeral 2 denotes a resonance plate made of a material having a resonant frequency lower than that of the piezoelectric element 1, a high plate thickness precision, and low ultrasonic attenuation. This resonance plate 2 and the piezoelectric element 1 are stuck together. The resonance plate 2 is supported at its periphery by a probe case or a supporting member. Numeral 3 denotes wires connected to electrode plates disposed on both surfaces of the piezoelectric element 1 in the thickness direction. Numeral 4 denotes a wiring plate for connecting the wire 3 to a cable 5, which in turn connects a probe to a main body of an ultrasonic apparatus which is not illustrated. Numeral 6 denotes a probe case. In the ultrasonic apparatus having the configuration heretofore described, a high voltage is supplied from the main body of the ultrasonic apparatus to the piezoelectric element 1 to cause the piezoelectric element 1 resonate. From the resonance of the piezoelectric element 1, complex resonance of the resonance plate 2 is generated. Ultrasonic waves having a plurality of frequencies caused thereby are transmitted into the object to be inspected. Ultrasonic waves transmitted through the object to be inspected or an ultrasonic echo reflected within the object to be inspected is measured.

Instead of the configuration heretofore described, a lens which is an object for focusing or diffusing ultrasonic beams transmitted from the probe and which is small in frequency dependence may be disposed between the resonance plate 2 and the probe case 6.

An ultrasonic probe according to the present invention will now be described in more detail by referring to an example. In this example, lead titanate (PbTiO3) ceramics having a resonant frequency formed to have an effective diameter and a thickness of 0.06 mm is used as the piezoelectric element. This piezoelectric element 1 and the resonance plate 2 made of a glass plate having a thickness of 0.8 mm are stuck together with an epoxy adhesive. The glass used as the resonance plate 2 has an acoustic propagation velocity of 5,600 m/s. The thickness of 0.8 mm has been chosen so that the resonant frequency will become 3.5 MHz when converted in terms of half wavelength.

Figure 2:
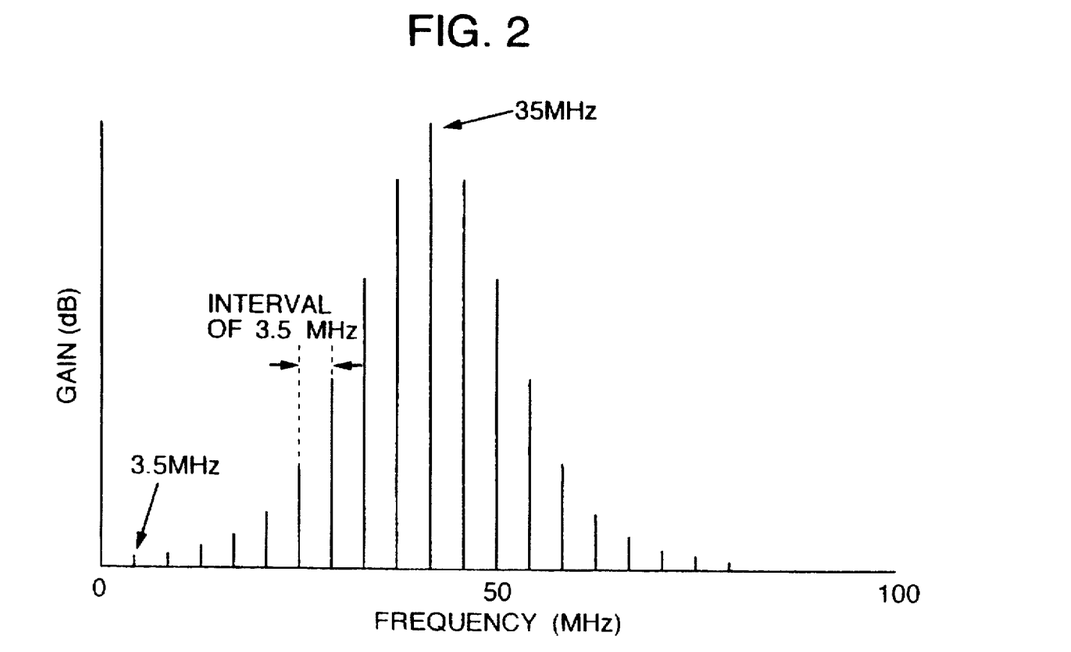
FIG. 2 is a diagram showing an example of a frequency spectrum of an ultrasonic wave transmitted to/received from an ultrasonic probe according to the present invention.

If this ultrasonic probe is driven with a pulse voltage or by continuously applying a voltage, complex resonance is caused in the resonance plate 2. In the frequency region of 1 MHz to 100 MHz as shown in FIG. 2, the complex resonance has a frequency spectrum at 3.5 MHz, which is the resonant frequency of the piezoelectric element 1, and a plurality of comb-shaped frequency spectra at intervals of 3.5 MHz in both the high frequency region and the low frequency region around 35 MHz.

In the above described configuration, an ultrasonic wave having frequencies of 3.5 MHz, 7 MHz, . . . . 35 MHz, . . . . , 66.5 MHz, . . . are outputted. In other words, a wideband ultrasonic wave of several MHz order to several tens MHz order is outputted from the ultrasonic probe according to the present invention. Comparing this with a conventional probe capable of outputting an ultrasonic wave of at most several MHz to ten and several MHz, it is evident that there is a significant difference in bandwidth.

Figure 3:
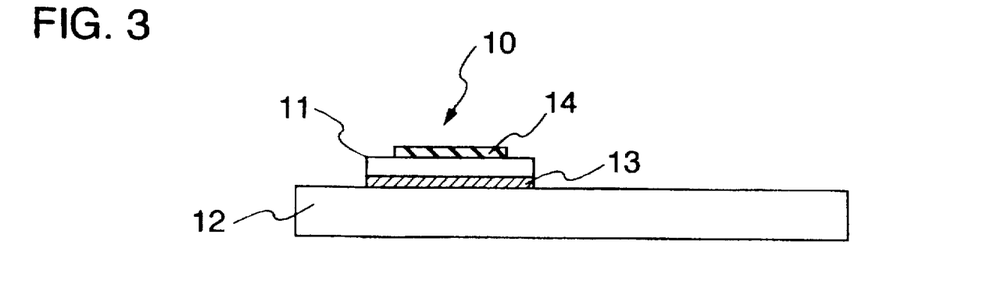
FIG. 3 is a diagram showing another embodiment of an ultrasonic probe according to the present invention.

FIG. 3 shows another embodiment of an ultrasonic probe according to the present invention. In FIG. 3, numeral 12 denotes a resonance plate. The resonance plate 12 is made of quartz glass having a thickness of 0.6 mm. The quartz glass has an acoustic propagation velocity of 5,960 m/s. Its resonant frequency has a value of 5 MHz when converted in terms of half wavelength. On one surface of the resonance plate 12, a lower electrode 13 is formed. The lower electrode 13 is a thin film containing gold/chromium formed by using the vacuum evaporation method. On this lower electrode 13, a piezoelectric thin film 11 is formed by using the high-frequency magnetron sputtering method. In the same way as the lower electrode 13, a thin film containing gold/chromium is formed on the other surface of the piezoelectric thin film 11 as an upper electrode 14 by using the vacuum evaporation method. In the present example, the piezoelectric thin film 11 has a thickness of 15 μm. A piezoelectric element 10 formed by the piezoelectric thin film 11, the lower electrode 13, and the upper electrode 14 has a resonant frequency corresponding to 100 MHz.

If the piezoelectric element 10 is driven in the present embodiment, complex resonance is caused in the resonance plate 12. In the frequency region of at least 1 MHz to 200 MHz in the same way as the case of FIG. 2, the complex resonance has a frequency spectrum of 100 MHz and a plurality of comb-shaped frequency spectra at intervals of approximately 5 MHz in both the high frequency region and the low frequency region around 100 MHz.

If the ultrasonic probe heretofore described is used, an ultrasonic wave in a frequency range of several MHz order to a frequency range of several hundreds MHz order can be transmitted to an object to be inspected simultaneously with a single ultrasonic probe to measure inside of the object to be inspected.

Figure 4:
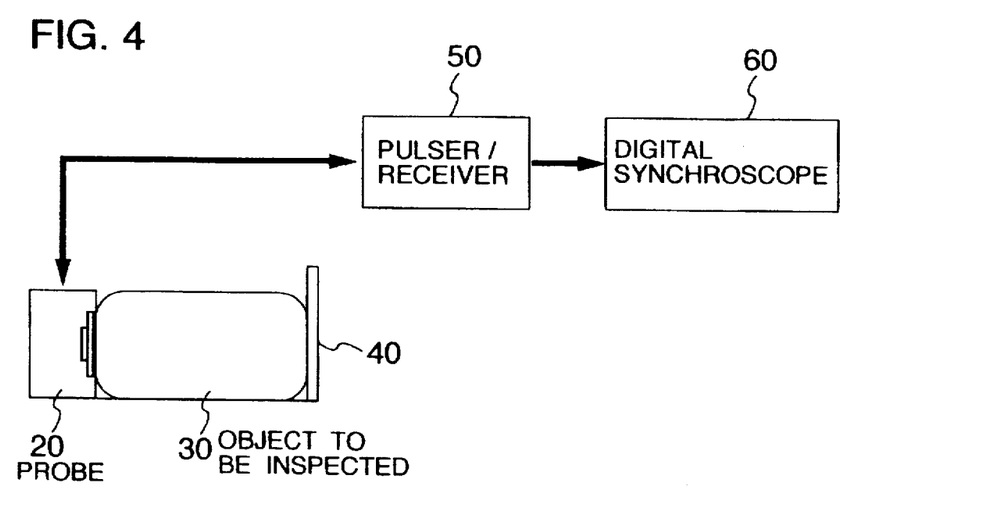
FIG. 4 is a diagram showing an embodiment of an apparatus for measuring an attenuation factor of an object to be inspected by using an ultrasonic probe of the present invention.

Several representative utilization methods of the ultrasonic probe according to the present invention will now be described. FIG. 4 shows an embodiment of an apparatus for measuring an ultrasonic attenuation factor of a living body by using an ultrasonic probe according to the present invention. In FIG. 4, numeral 20 denotes the above described ultrasonic probe. Numeral 30 denotes an object to be inspected. Numeral 40 denotes a full reflector for reflecting ultrasonic waves perfectly. Numeral 50 denotes a transmitting/receiving circuit. The transmitting/receiving circuit 50 drives the ultrasonic probe 20 to transmit an ultrasonic wave into the object to be inspected in a pulsative form. In addition, the transmitting/receiving circuit 50 detects the ultrasonic wave transmitted through the object to be inspected, reflected by the full reflector 40, and received by the ultrasonic probe 20. Numeral 60 denotes an analyzing unit including a digital synchroscope.

Operation of the apparatus shown in FIG. 4 will now be described. In order to transmit ultrasonic waves into the object 30 to be inspected, a pulse signal for driving a piezoelectric element included in the ultrasonic probe 20 is generated by a pulse generation circuit included in the transmitting/receiving circuit 50. This pulse signal is applied to an electrode of the piezoelectric element. Thus the piezoelectric element vibrates with, for example, the above described frequency of 35 MHz and complex resonance is caused in a resonance plate stuck to the piezoelectric element. Thereby, ultrasonic waves having a plurality of frequency spectra around a center frequency of 35 MHz as shown in FIG. 2 are transmitted into the object 30 to be inspected.

The ultrasonic waves transmitted into the object 30 to be inspected are propagated through the living body while being attenuated in association with the ultrasonic attenuation factor of the tissue within the object 30 to be inspected, reflected perfectly by the full reflector 40, propagated again to the ultrasonic probe 20 while being attenuated, and received by the probe 20. The ultrasonic waves received by the probe 20 are converted into electric signals, detected by the transmitting/receiving circuit 50, and sent to the analyzing unit 60.

In the analyzing unit 60, the attenuation factor of the living body is analyzed as hereafter described. Representing the resonant frequency by ω, a transmitting/receiving frequency response function of the complex resonance ultrasonic probe by $H_t(\omega)$, and a frequency response including the reflection characteristic of the living body by $H_b(\omega)$, a full response function $H(\omega)$ of a system driven in an impulsive form is represented as $$H(\omega)=H_t(\omega)H_b(\omega) \quad (1)$$

Since $H(\omega)$ is the received waveform spectrum itself of this system, it is a measured value. Since $H_t(\omega)$ can be derived analytically from the admittance characteristic of the complex resonance ultrasonic probe, the frequency response of the living body is derived from the received waveform spectrum which is the measured value and the transmitting/receiving frequency response function of the complex resonance ultrasonic probe which is the analytic value on the basis of the following relation.

$$H_b(\omega)=H(\omega)/H_t(\omega) \quad (2)$$

In the transmitting/receiving frequency response function of the complex resonance ultrasonic probe, the transmitting characteristic has the same frequency response characteristic as a comb filter on the frequency domain. Representing a complex resonant frequency by $\omega_i$ and an amplitude by $C_i$, the transmitting/receiving frequency response function $H_t(\omega)$ of the complex resonance ultrasonic probe is given by the following relation.

$$H_t(\omega)=\Sigma C_i\delta(\omega-\omega_i) \quad (3)$$

In such a configuration that a reflection plate which can be regarded as a full reflector is installed on the back of a sample, the frequency response of the living body is mainly determined by only attenuation depending on the frequency.

Representing a frequency dependent attenuation factor of the living body by α and a depth of the reflection plate from the probe by d, the frequency response $H_b(\omega)$ of the living body including the reflection characteristic is represented by the following relation.

$$H_b(\omega)=\exp(-2\alpha\omega d) \quad (4)$$

From equation (2), the following relation is derived.

$$\exp(-2\alpha\omega d)=H(\omega)/(\Sigma C_i\delta(\omega-\omega_i)) \quad (5)$$

By comparing sides of the equation (5) with each other, an attenuation constant $\alpha(\omega_i)$ in each frequency can be derived as shown in equation (6).

$$\alpha(\omega_i)=(-\frac{1}{2}\omega_i d)*ln\{H(\omega_i)/(\Sigma C_i\delta(\omega-\omega_i))\} \quad (6)$$

In other words, the attenuation factor of a tissue of the living body can be derived by the analyzing unit 60 on the basis of the equations (1) through (6) heretofore described. By deriving this attenuation factor, the difference of physical characteristics of tissues of the living body can be used for diagnosis. For example, stiffness of an object, i.e., difference in density and component can be measured. An unequal object in an uniform tissue can thus be found.

Figure 5:
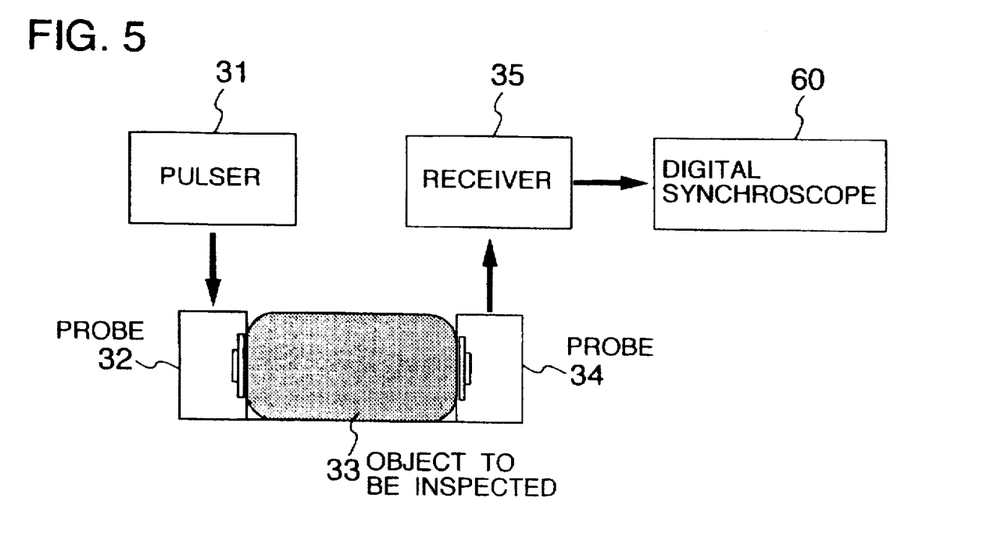
FIG. 5 is a diagram showing another embodiment of an apparatus for measuring an attenuation factor of an object to be inspected by using an ultrasonic probe of the present invention.

Alternatively in the example of measurement of the ultrasonic attenuation factor in the object to be inspected as shown in FIG. 4, the ultrasonic attenuation factor of the living body may be measured with the ultrasonic transmission method by using the probe of the present invention instead of the ultrasonic full reflector 40. In other words, instead of such a configuration that transmission and reception are conducted by using the same ultrasonic probe, transmission and reception can be conducted by using different ultrasonic probes having the same configuration. If this ultrasonic transmission method is used, a configuration shown in FIG. 5 is obtained. A signal generated by a transmission circuit 31 is applied to a first probe 32. Ultrasonic waves are transmitted into an object 33 to be inspected. The ultrasonic waves transmitted through the object to be transmitted are received by a second probe 34, converted into electric signals, detected by a receiving circuit 35, and sent to the analyzing unit 60. The attenuation factor can be derived in this analyzing unit 60. If scanning of the object to be inspected by using this transmission method is combined with the image reconstruction method used in the known X-ray CT as a medical image diagnostic apparatus, an ultrasonic CT apparatus becomes possible.

Figure 6:
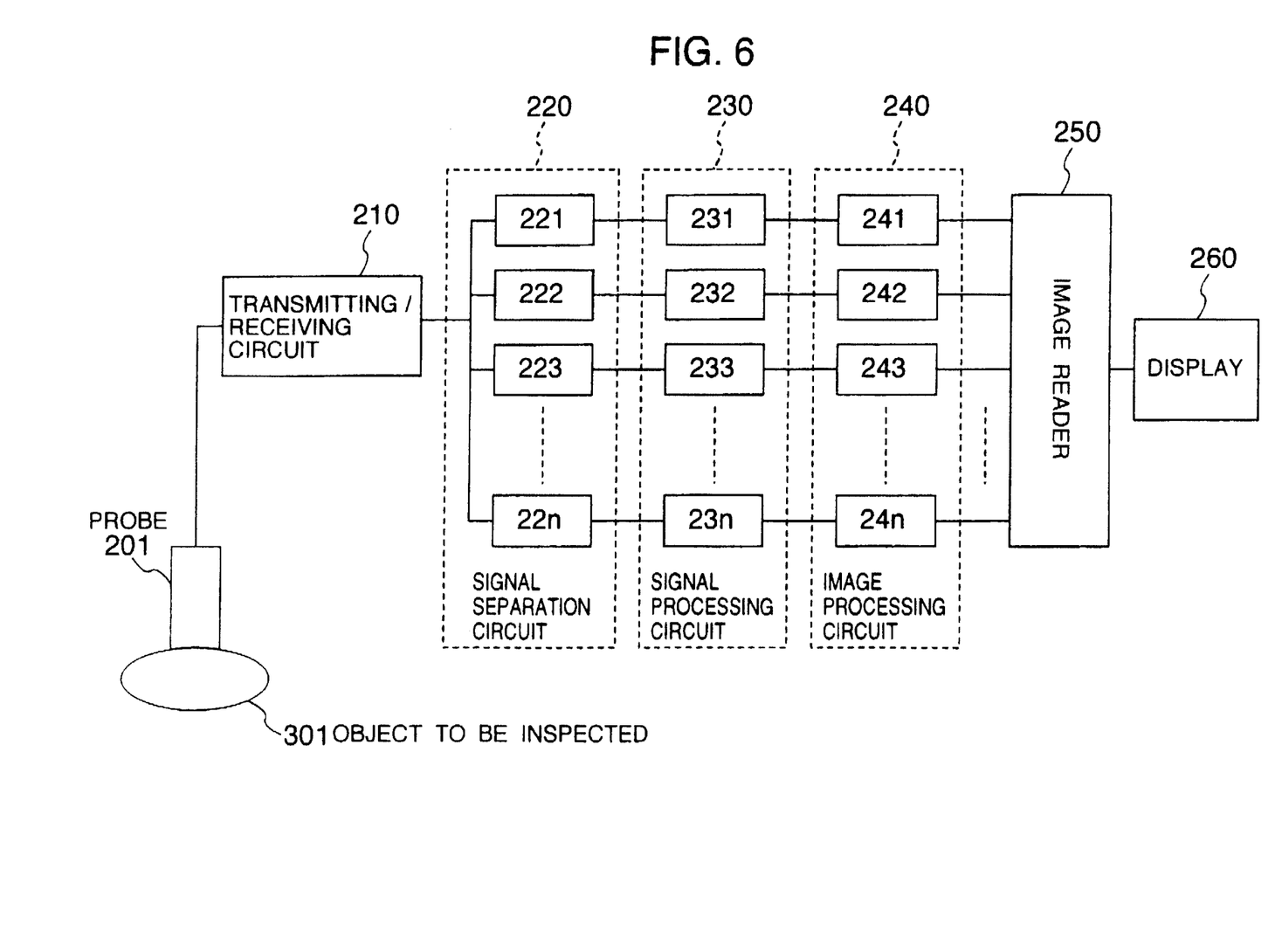
FIG. 6 is a diagram showing an embodiment of an apparatus for obtaining images of a plurality of frequencies in a single scan by using an ultrasonic probe of the present invention.

An embodiment using an ultrasonic probe of the present invention for imaging in the object to be inspected will now be described by referring to FIG. 6. In FIG. 6, numeral 201 denotes an ultrasonic probe using the present invention. This probe 201 is configured so that the object 301 to be inspected may be scanned with ultrasonic beams. For the scanning with the ultrasonic beams, a configuration for mechanically moving the probe as shown in FIG. 1 or such a configuration having a large number of complex resonance piezoelectric elements shown in FIG. 1 arranged in an array form may be adopted. Numeral 210 denotes a transmitting/receiving circuit, which generates a pulse for driving the ultrasonic probe 201 and generates beam-like echo signals from ultrasonic waves received by the probe 201. Numeral 220 denotes a signal separation circuit for separating signals inputted from the transmitting/receiving circuit 210 into signals of respective frequencies by using a plurality of filters 221, 222, ..., 22n. Numeral 230 denotes a signal processing circuit for conducting signal processing such as logarithmic compression and detection on signals supplied from the transmitting/receiving circuit 210. This signal processing circuit is disposed as 231, 232, ..., 23n respectively succeeding the filters 221, 222, ..., 22n. Numeral 240 denotes an image processing circuit. In the present field, the image processing circuit is one called digital scan converter. The image processing circuit is also installed so as to succeed respective signal processing circuits as 241, 242, ..., 24n. Numeral 250 denotes an image reader for switching over and reading out outputs of the image processing circuit 240. Numeral 260 denotes a display unit for image display such as a CRT.

In the above described configuration, a plurality of images are simultaneously obtained from the same section of the object to be inspected by conducting a single scan with respect to the object to be inspected with ultrasonic beams supplied from a single probe. Hereafter, its operation will be described. From the probe 201 driven by a pulse signal supplied from the transmitting/receiving circuit 210, ultrasonic beams are transmitted into the object 301 to be inspected. In a boundary within the object to be inspected between regions which are different in acoustic impedance, the ultrasonic waves are reflected. Echo signals are received by the probe 201. In the transmitting/receiving circuit 210, electric signals of the received ultrasonic beams are formed. The signals are inputted to the signal separation circuit 220. By the filters 221, 222, ..., 22n, echo signals having specific frequencies respectively corresponding to a plurality of ultrasonic frequencies transmitted from the probe 201 are taken out.

Respective echo signals taken out are subjected to logarithmic compression and detection respectively in the signal processing circuits 231 to 23n and inputted to the image processing circuits, respectively. In the image processing circuit 240, inputted signals are converted to digital signals and stored in respective circuits. In the image processing circuit 240, the attenuation factor is calculated as occasion demands.

The series of operations heretofore described are executed in order each time the radiation direction or the radiation position of the ultrasonic beams is changed. The inside of the object to be inspected is scanned by ultrasonic beams. Image data are successively taken into the image processing circuit 240. When one scan is completed, image data corresponding to one image are written into each of the image processing circuits 241 to 24n, respectively.

When image data have been written into the image processing circuit 240, the operator operates the image reader 250 to display an image of a desired frequency on the display unit 260 and observe it. In other words, the operator operates the image reader 250 so as to display an image generated by using a high frequency signal on the display unit 260 when observing a region shallow from the surface of the object to be inspected and display an image created by using a low frequency signal when observing a deep region. Unlike the conventional technique, therefore, it becomes unnecessary to exchange probes having different frequencies depending upon whether the region is a deep portion or shallow portion of the object to be inspected in taking in ultrasonic images. Alternatively in the embodiment heretofore described, an image synthesizer may be installed in place of the image reader 250 or in parallel with the image reader 250. In this case, a plurality of images generated by the image processing circuits 241 to 24n are displayed side by side on the screen of the display unit 260 by the image synthesizer.

Figure 7:
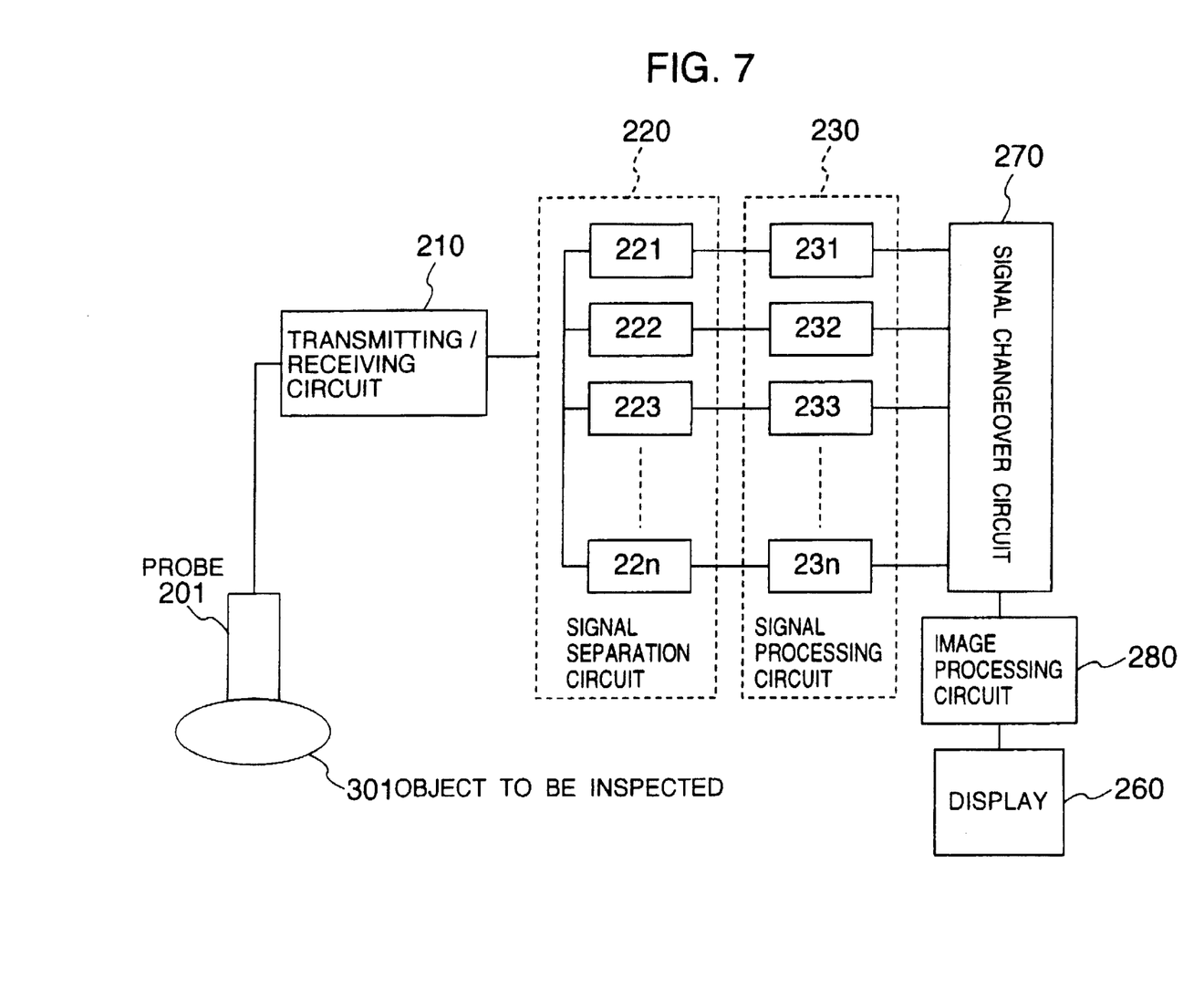
FIG. 7 is a diagram showing an embodiment of an apparatus for obtaining images of frequencies which are different region from region in the depth direction of the object to be inspected, in a single scan by using an ultrasonic probe of the present invention.

Another embodiment of an ultrasonic probe used for imaging the inside of the object to be inspected according to the present invention will now be described by referring to FIG. 7. The present embodiment differs from the embodiment of FIG. 6 in that a signal changeover circuit 270 is disposed in a stage succeeding the signal processing circuit 230. The output of this signal changeover circuit 270 is inputted to a single image processing circuit 280. Image data generated by the image processing circuit 280 are outputted to the display unit 260.

Operation of the embodiment shown in FIG. 7 will now be described. Ultrasonic waves are transmitted from the probe 201 into the object 301 to be inspected. Echo signals are received. Received ultrasonic beams are generated by the transmitting/receiving circuit 210. The signals are inputted to the signal separation circuit 220 and divided therein into a plurality of frequency signals. Thereafter, those signals are subjected to logarithmic compression and detection in the signal processing circuit 230. The operation is conducted so far in the same way as the embodiment of FIG. 6. Output signals of the signal processing circuits 231, 232, ..., 23n are linked by the signal changeover circuit 270 in a time division manner, and outputted to the image processing circuit 280 as a single received ultrasonic beam signal. In other words, a signal having the highest frequency and capable of displaying the shallowest region with the highest resolution is first outputted from the signal processing circuit 231 for a predetermined time. A signal having the next highest frequency and capable of displaying the next shallowest region with the next highest resolution is then outputted from the signal processing circuit 231 for the predetermined time. Thereafter, lower frequency signals are successively outputted each for the predetermined time. Signals thus outputted are successively converted to images by the signal processing circuit 280.

To speak in plain language, the object to be inspected corresponding to a single ultrasonic image is divided into a plurality of regions from the shallowest region to the deepest region. The shallowest region is imaged by using the highest frequency signal. As the depth becomes larger, the region is imaged by using a lower frequency signal. By doing so, a single image is obtained in the same time as the conventional apparatus requires, and respective regions in the depth direction can be imaged with signals having the best resolution.

In each of the above described embodiments, the resonant frequency of the piezoelectric element is chosen to be 35 MHz or 100 MHz. Alternatively, a higher frequency such as an arbitrary value in the range of 150 MHz to 500 MHz may be chosen. If in this case the resonant frequency of the complex resonance plate is set to that value determined with a conversion in terms of half wavelength corresponding to the plate thickness, it becomes possible to generate complex resonance having a plurality of frequency spectra effective as an ultrasonic signal in the frequency region of several MHz to several hundreds MHz.

In the preferred embodiments above mentioned, a basic structure of the ultrasonic probe is explained as one channel probe having one piezoelectric element. However, a multi-channel ultrasonic probe can be constructed by arranging a plurality of piezoelectric elements each having the same structure as that of the piezoelectric element shown in FIG. 1A or FIG. 3.

The present invention is not limited to the embodiments, but various modifications encompassed by the claims are included in the present invention.

We claim:

1. An ultrasonic probe comprising:

a piezoelectric element having a first resonant frequency; and a complex resonance member stuck to said piezoelectric element, said complex resonance member having a second resonant frequency different from said first resonant frequency, said complex resonance member at least one of inputting and outputting an ultrasonic wave of said first resonant frequency and a plurality of other frequencies.

2. An ultrasonic probe according to claim 1, wherein said complex resonance member has said second resonant frequency determined with conversion in terms of half wavelength.

3. An ultrasonic probe according to claim 1, wherein said complex resonance member comprises a resonance portion at least one of inputting and outputting said ultrasonic wave, said ultrasonic wave having a plurality of frequency spectra located at predetermined frequency intervals in both a higher frequency region and a lower frequency region around said first resonant frequency.

4. An ultrasonic probe according to claim 3, wherein said ultrasonic wave has a plurality of frequency spectra located at intervals equivalent to said second resonant frequency.

5. An ultrasonic probe according to claim 1, wherein said piezoelectric element comprises a piezoelectric element containing lead titanate ceramics, and said complex resonance member comprises a resonance portion containing a glass member.

6. An ultrasonic probe according to claim 1, wherein said piezoelectric element comprises:

an electrode containing a conductive member; and a piezoelectric film formed on said electrode.

7. An ultrasonic probe according to claim 6, wherein said piezoelectric element comprises a thin film electrode containing at least one of gold and chromium.

8. An ultrasonic inspection apparatus comprising:

an ultrasonic probe including a piezoelectric element having a first resonant frequency, and a complex resonance member stuck to said piezoelectric element, said complex resonance member having a second resonant frequency different from said first resonant frequency, said complex resonance member at least one of inputting and outputting an ultrasonic wave of said first resonant frequency and a plurality of other frequencies;

means for driving said ultrasonic probe and thereby at least one of transmitting and receiving said ultrasonic wave of the plurality of frequencies at least one of to and from an object to be inspected; and means for measuring, from received signals, attenuation applied to said ultrasonic wave of the plurality of frequencies by said object to be inspected.

9. An ultrasonic inspection apparatus comprising:

first and second ultrasonic probes, each including a piezoelectric element having a first resonant frequency, and a complex resonance member stuck to said piezoelectric element, said complex resonance member having a second resonant frequency different from said first resonant frequency, said complex resonance member at least one of inputting and outputting an ultrasonic wave of said first resonant frequency and a plurality of other frequencies, said first and second ultrasonic probes facing each other with an object to be inspected between, said first ultrasonic probe transmitting said ultrasonic wave, said second ultrasonic probe receiving said ultrasonic wave;

means for driving said first ultrasonic probe and thereby transmitting said ultrasonic wave of the plurality of frequencies to an object to be inspected; and means for measuring, from ultrasonic signals of the plurality of frequencies received by said second ultrasonic probe, attenuation applied to said ultrasonic wave of the plurality of frequencies by said object to be inspected.

10. An ultrasonic inspection apparatus comprising:

an ultrasonic probe including a piezoelectric element having a first resonant frequency, and a complex resonance member stuck to said piezoelectric element, said complex resonance member having a second resonant frequency different from said first resonant frequency, said complex resonance member at least one of inputting and outputting an ultrasonic wave of said first resonant frequency and a plurality of other frequencies;

means for driving said ultrasonic probe and thereby at least one of transmitting and receiving said ultrasonic wave of the plurality of frequencies at least one of to and from an object to be inspected, and scanning said object to be inspected with ultrasonic beams;

signal separation means for separating signals received by a receiving means into a plurality of signals according to frequency for each ultrasonic beam;

image processing means for conducting image processing on signals outputted from said signal separation means for each of the signals with the same frequency and generating a plurality of sheets of image data; and means for displaying an output signal of said image processing means as an image.

11. An ultrasonic inspection apparatus according to claim 10, further comprising image selection means for selecting an image associated with a specific frequency from said image processing means and causing said displaying means to display said selected image.

12. An ultrasonic inspection apparatus comprising:

an ultrasonic probe including a piezoelectric element having a first resonant frequency, and a complex resonance member stuck to said piezoelectric element, said complex resonance member having a second resonant frequency different from said first resonant frequency, said complex resonance member at least one of inputting and outputting an ultrasonic wave of said first resonant frequency and a plurality of other frequencies;

means for driving said ultrasonic probe and thereby at least one of transmitting and receiving said ultrasonic wave of the plurality of frequencies at least one of to and from an object to be inspected, and scanning said object to be inspected with ultrasonic beams;

signal separation means for separating signals received by a receiving means into a plurality of signals according to frequency for each ultrasonic beam;

image processing means for constructing images using signals of different frequencies among the signals separated according to depth in said object to be inspected; and means for displaying an output signal of said image processing means as an image.

13. An ultrasonic inspection apparatus according to claim 12, wherein said image processing means comprises means for imaging a shallow region of said object to be inspected by using a high frequency signal and imaging a deeper region by using a lower frequency signal.

14. An ultrasonic inspection apparatus according to claim 12, wherein said signal separation means comprises signal changeover means for outputting said plurality of signals separated to said image processing means in a predetermined order for a predetermined time.

15. An ultrasonic inspection apparatus according to claim 14, wherein said signal changeover means comprises means for outputting frequencies in an order of magnitude of frequency.

16. An ultrasonic inspection apparatus comprising:

an ultrasonic probe for at least one of inputting and outputting an ultrasonic wave having a plurality of frequency spectra in a frequency range of several MHz to several hundreds MHz;

means for driving said ultrasonic probe and thereby at least one of transmitting and receiving said ultrasonic wave at least one of to and from an object to be inspected; and means for measuring, from a received signal, attenuation applied to said ultrasonic wave of the plurality of frequencies by said object to be inspected.

17. An ultrasonic inspection apparatus according to claim 16, wherein said ultrasonic probe comprises:

piezoelectric element having a first resonant frequency; and a complex resonance member stuck to said piezoelectric element, said complex resonance member having a second resonant frequency different from said first resonant frequency, said complex resonance member at least one of inputting and outputting an ultrasonic wave of said first resonant frequency and a plurality of other frequencies.

18. An ultrasonic inspection apparatus comprising:

first and second ultrasonic probes respectively at least one of inputting and outputting an ultrasonic wave having a plurality of frequency spectra in a frequency range of several MHz to several hundreds MHz, said first and second ultrasonic probes facing each other with an object to be inspected between, said first ultrasonic probe transmitting said ultrasonic wave, said second ultrasonic probe receiving said ultrasonic;

means for driving said first ultrasonic probe and thereby transmitting said ultrasonic wave of the plurality of frequencies to an object to be inspected; and means for measuring, from ultrasonic signals of the plurality of frequencies received by said second ultrasonic probe, attenuation applied to said ultrasonic wave of the plurality of frequencies by said object to be inspected.

19. An ultrasonic inspection apparatus according to claim 18, wherein each of said first and second ultrasonic probes comprises:

a piezoelectric element having a first resonant frequency; and a complex resonance member stuck to said piezoelectric element, said complex resonance member having a second resonant frequency different from said first resonant frequency, said complex resonance member at least one of inputting and outputting an ultrasonic wave of said first resonant frequency and a plurality of other frequencies.

20. An ultrasonic inspection apparatus comprising:

an ultrasonic probe for at least one of inputting and outputting an ultrasonic wave having a plurality of frequency spectra in a frequency range of several MHz to several hundreds MHz;

means for driving said ultrasonic probe and thereby at least one of transmitting and receiving said ultrasonic wave of the plurality of frequencies at least one of to and from an object to be inspected, and scanning said object to be inspected with ultrasonic beams;

signal separation means for separating signals received by a receiving means into a plurality of signals according to frequency for each ultrasonic beam;

image processing means for conducting image processing on signals outputted from said signal separation means for each of the signals with the same frequency and generating a plurality of sheets of image data; and means for displaying an output signal of said image processing means as an image.

21. An ultrasonic inspection apparatus according to claim 20, wherein said ultrasonic probe comprises:

a piezoelectric element having a first resonant frequency; and a complex resonance member stuck to said piezoelectric element, said complex resonance member having a second resonant frequency different from said first resonant frequency, said complex resonance member at least one of inputting and outputting an ultrasonic wave of said first resonant frequency and a plurality of other frequencies.

22. An ultrasonic inspection apparatus comprising:

an ultrasonic probe for at least one of inputting and outputting an ultrasonic wave having a plurality of frequency spectra in a frequency range of several MHz to several hundreds MHz, means for driving said ultrasonic probe and thereby at least one of transmitting and receiving said ultrasonic wave of the plurality of frequencies at least one of to and from an object to be inspected, and scanning said object to be inspected with ultrasonic beams;

signal separation means for separating signals received by a receiving means into a plurality of signals according to frequency for each ultrasonic beam;

image processing means for constructing images using signals of different frequencies among the signals separated according to depth in said object to be inspected; and means for displaying an output signal of said image processing means as an image.

23. An ultrasonic inspection apparatus according to claim 22, wherein said image processing means comprises means for imaging a shallow region of said object to be inspected by using a high frequency signal and imaging a deeper region by using a lower frequency signal.

24. An ultrasonic inspection apparatus according to claim 22, wherein said ultrasonic probe comprises:

a piezoelectric element having a first resonant frequency; and a complex resonance member stuck to said piezoelectric element, said complex resonance member having a second resonant frequency different from said first resonant frequency, said complex resonance member at least one of inputting and outputting an ultrasonic wave of said first resonant frequency and a plurality of other frequencies.

25. An ultrasonic inspection apparatus according to claim 22, wherein said signal separation means comprises signal changeover means for outputting said plurality of separated frequencies to said image processing means in a predetermined order for a predetermined time.

26. An ultrasonic inspection apparatus according to claim 25, wherein said signal changeover means comprises means for outputting frequencies to said image processing means in an order of magnitude of frequency.

27. An ultrasonic probe according to claim 1, wherein said first resonant frequency of said piezoelectric element is a maximum frequency and said second resonant frequency of said complex resonance member is a minimum frequency in a frequency band utilized.

* * * * *